United States Patent [19]

Beineke

[11] Plant 4,968

[45] Dec. 28, 1982

[54] BLACK WALNUT TREE

[75] Inventor: Walter F. Beineke, West Lafayette, Ind.

[73] Assignee: Purdue Research Foundation, West Lafayette, Ind.

[21] Appl. No.: 254,904

[22] Filed: Apr. 16, 1981

[51] Int. Cl.[3] ..... A01H 5/03

[52] U.S. Cl. ..... Plt./32

[58] Field of Search ..... Plt./32

*Primary Examiner*—Robert E. Bagwill

*Attorney, Agent, or Firm*—John R. Nesbitt

[57] ABSTRACT

A new and distinct cultivar of black walnut tree (*Juglans nigra L.*) which is distinctly characterized by outstanding nut qualities, such as abundant annual crops of average-sized nuts, begins nut-bearing very early in life of tree, averages 4 nuts per cluster, and produces kernels which exceed about fifteen (15) percent of nut weight. The nuts are medium-sized and ripen mid-season. The new variety is very late in time of leafing and has excellent walnut anthracnose resistance. The pistillate flowers mature very late and pollen maturity is late. In most years there is little overlap in female and male flowering. This variety has fairly slow growth and poor straightness. Flowering begins very early in the life of the tree. This new variety of black walnut tree was discovered by the applicant near Bentonville in Fayette County, Ind., in a cultivated area. In occurred as a wild tree growing on land managed for timber-growing purposes and was discovered in the course of a search for unique and high quality black walnut trees to be utilized in breeding for outstanding timber producing potential. This selection has been designated as BW13 in records maintained on the performance of grafts made from the original selection and will be known henceforth as Fayette-2.

3 Drawing Figures

BACKGROUND OF THE INVENTION

Figure 1:
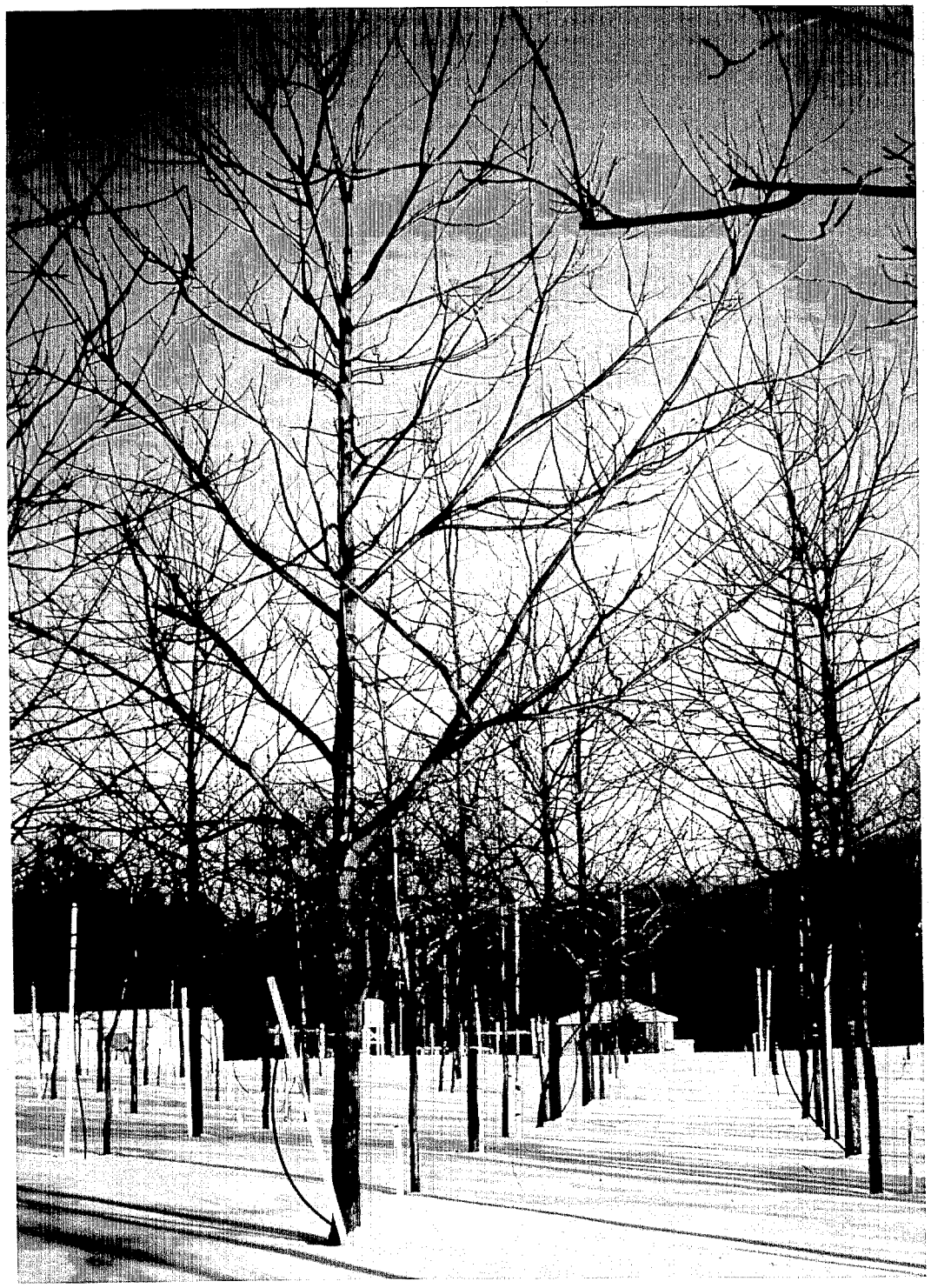
FIG. 1 is a photograph showing the timber form of Fayette-2.
Figure 2:
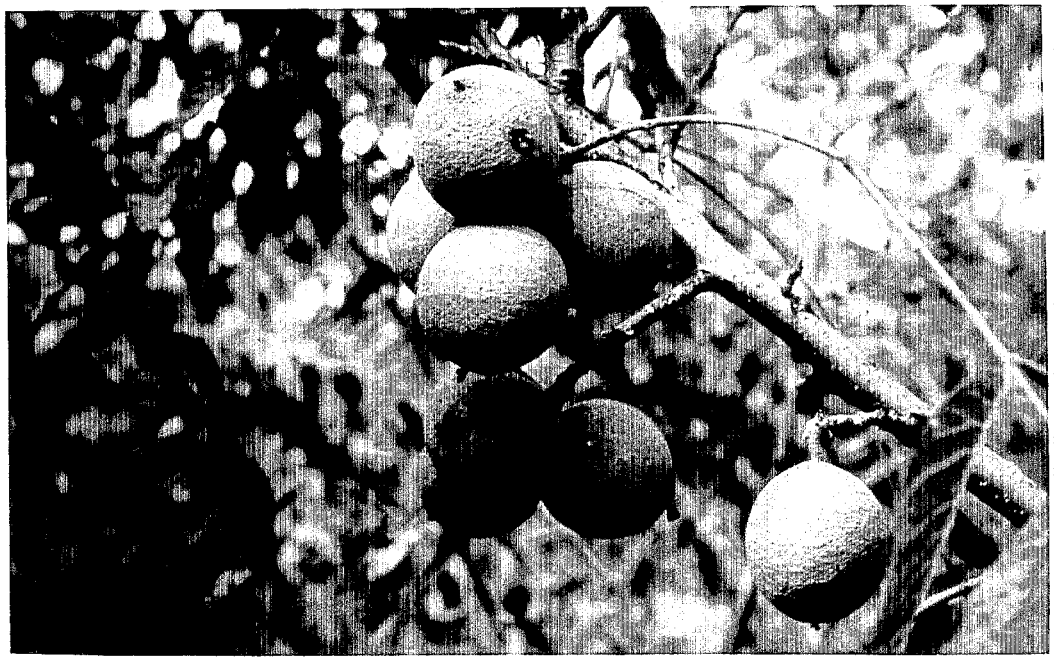
FIG. 2 is a photograph showing a twig with nuts attached from Fayette-2.
Figure 3:
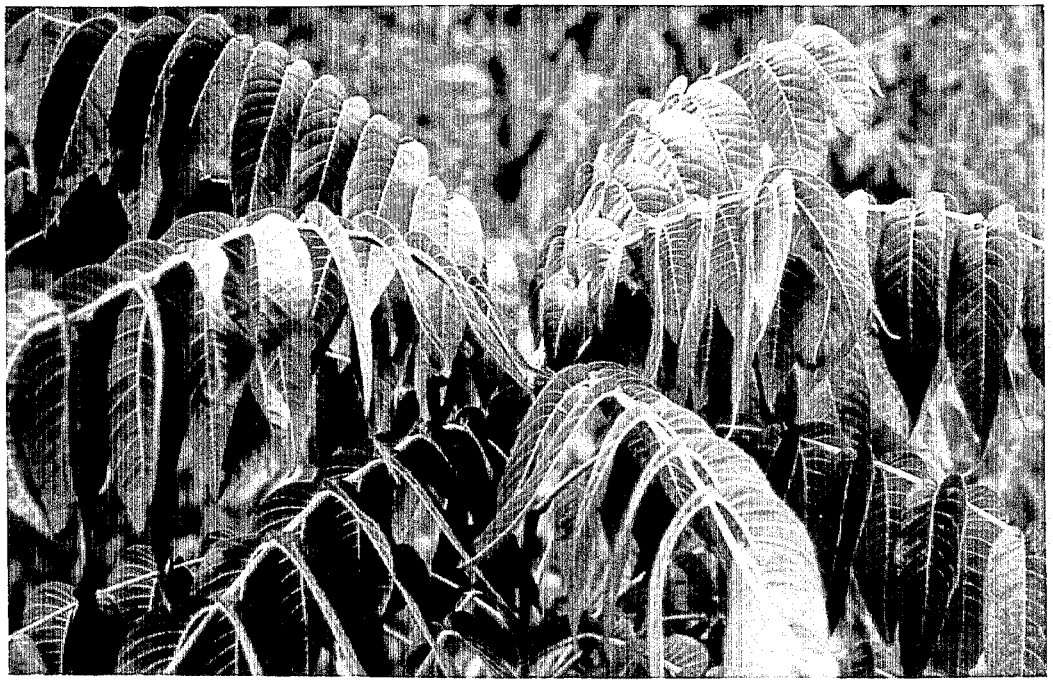
FIG. 3 is a photograph showing leaves from Fayette-2.

After the original clone was selected, and assigned an identity number of BW13, the aforesaid tree was reproduced by collecting scions from it and grafting these onto common black walnut rootstocks at Martell Forest, Purdue University. These asexual reproductions ran true to the parent tree and to each other in all respects.

The botanical details of this new and distinct variety of walnut tree are as follows:

Tree:

*Size.*—Large.

*Vigor.*—Vigorous.

*Growth rate.*—Slower than Purdue 1-6% smaller in diameter than the average of selected clones planted the same year, 2% shorter than the average, and 12% less cubic foot volume than the average.

*Form.*—Poor timber form — 41% below average in straightness on a rating scale of 1 to 5. Many crooks.

Trunk:

*Bark.*—Dark brown to gray.

*Texture.*—Interlacing ridges.

Branches:

*Diameter.*—Large.

*Length.*—Long.

*Branch angle.*—Lower branches — steep — 66 deg.

*Foliage.*—Quantity — Abundant. Density — Heavy.

Leaves:

*Compound leaves.*—Size — shorter than average; average length — 15⅛".

*Leaflets.*—Size — Large; average length — 4¾"; average width — 1½"; average number of leaflets — 18; shape — lanceolate; acutely pointed. Thickness — thin; Texture — smooth; Margin — serrated; Petiole — short; Color — Topside — dark green; Underside — light green.

*Anthracnose resistance.*—Excellent much better than average on a rating scale of 1 to 5.

*Timing of leafing.*—Very late — averages 11 to 12 days later or 110% later than average.

Flowering habit:

*Age at which tree starts producing catkins.*—Very early.

*Number of catkins produced.*—Abundant.

*Size of catkins.*—Average.

*Time of pollen shed.*—Late.

*Age at which time tree starts producing pistillate flowers.*—Very early.

*Number of pistillate flowers produced by young trees-*.—Abundant.

*Number of pistillate flowers produced by mature trees.*—Abundant.

*Lateral shoots producing pistillate flowers.*—Abundant.

*Number of pistillate flowers per inflorescence.*—5.

*Timing of pistillate flower receptivity.*—Very late.

*Coincidence of staminate and pistillate bloom.*—None.

Nut crop:

*Bearing.*—Annual.

*Productivity.*—Extremely heavy — Better than any other clone in the study.

*Ripening period.*—Mid-season.

*Evenness of maturity (period between first and last nuts are ready for harvest).*—Even.

*Quality.*—Excellent.

*Distribution of nuts on tree.*—Throughout.

Hull:

*Outer surface.*—Warty.

*Form.*—Round both ends.

*Thickness.*—Thin.

*Size.*—Small; average length — 2"; average diameter in suture plane — 1 13/16"; average diameter cheek to cheek — 1 15/16".

Nut:

*Size.*—Medium; average length — 1⅜"; average diameter in suture plane — 1 7/32"; average diameter cheek to cheek — 1⅜".

*Uniformity of size.*—Uniform.

*Form.*—Rounded.

*Blossom end.*—Rounded.

*Basal end.*—Rounded.

*Weight.*—Dry weight of ten nuts — 155.7 gm; dry weight of ten kernels — 23.8 gm; average percentage kernel to nut — 15.3%.

*Thickness of shell.*—Medium.

*Fill.*—Good.

Kernel:

*Size.*—Large.

*Plumpness.*—Plump.

*Shrivel.*—None.

*Flavor.*—Good.

*Color.*—Light.

The walnut tree and its nuts herein described may vary in slight detail due to climatic and soil conditions under which the variety may be grown; the present description being of the variety as grown near West Lafayette, Ind.

I claim:

1. A new and distinct variety of black walnut tree substantially as illustrated and described, which produces abundant annual crops of medium-size nuts; averaging 4 per cluster; the percentage of weight of kernel to nut averages approximately 15 percent, and nut bearing begins early in life of tree; time of leafing is much later than average and has excellent anthracnose resistance; pistillate flowers develop very late and pollen sheds late.

* * * * *